United States Patent [19]
Rüttimann

[11] Patent Number: 5,929,288
[45] Date of Patent: Jul. 27, 1999

[54] PROCESS FOR MANUFACTURING POLYENE ALDEHYDES

[75] Inventor: August Rüttimann, Arlesheim, Switzerland

[73] Assignee: Roche Vitamins Inc., Parsippany, N.J.

[21] Appl. No.: 08/865,288

[22] Filed: May 29, 1997

[30] Foreign Application Priority Data

Jun. 28, 1996 [EP] European Pat. Off. .............. 96110463

[51] Int. Cl.⁶ .................................................... C07C 45/60
[52] U.S. Cl. .......................... 568/447; 568/446; 568/449; 568/459
[58] Field of Search .................................................... 568/3

[56] References Cited

FOREIGN PATENT DOCUMENTS 1 541 972  1/1977  United Kingdom .

OTHER PUBLICATIONS

Greene et al; Protective Groups in Organic Synthesis, pp. 125–126, 1981.
Mukaiyama et al; Bull.Chem.Soc.(Japan),50(5),pp. 1161–1168, 1977.
I.N. Nazarov et al., J. Gen. Chem. USSR [Engl. Transl.], 28, pp. 2477–2483 (1958).
S. M. Makin et al., J. Gen. Chem. USSR [Engl. Transl.] 31, pp. 3096–3099 (1961).
S. M. Makin et al., J. Gen. Chem. USSR [Engl. Transl.] 32, pp. 3112–3114 (1962).
Zh. A. Krasnaya et al., J. Gen. Chem. USSR [Engl. Transl.] 32, pp. 63–68 (1962).
S.M. Makin, Pure & Appl. Chem. 47, pp. 173–181 (1976).
Chem. Abstract vol. 57, No. 13, Dec. 24, 1962, Abstract No. 16671c.
Chem. Abstract vol. 52, No. 14, Jul. 25, 1958, Abstract No. 17737c.

*Primary Examiner*—Shailendra Kumar
*Assistant Examiner*—Sreeni Padmanabhan
*Attorney, Agent, or Firm*—George W. Johnston; Dennis P. Tramaloni; Eileen M. Ebel

[57] ABSTRACT

To manufacture polyene aldehydes and polyene dialdehydes a polyene O,O-dialkyl acetal or polyene di(O,O-dialkyl acetal) is reacted with a 1-alkoxy-1,3-diene in the presence of a Lewis acid or a Brönsted acid. The reaction mixture is then hydrolyzed and the alcohol is cleaved under basic conditions from the polyene derivative produced by the reacting. Those intermediates in this process from which the alcohol is to be cleaved are novel. The final products are primarily carotenoids which can be used as colorants and pigments for foodstuffs, animal products, and the like.

21 Claims, No Drawings

PROCESS FOR MANUFACTURING POLYENE ALDEHYDES

BACKGROUND OF THE INVENTION

1. Field

The present invention is concerned with a novel process for the manufacture of polyene (di)aldehydes from acetalised short-chain polyene (di)aldehydes by an acid-catalyzed condensation reaction with alkoxydienes.

2. Description

Lewis acid-catalyzed additions of α,β-unsaturated ethers (enol ethers) to acetals have been known for a long time and date back to the work of Müller-Cunradi and Pieroh (see U.S. Pat. No. 2,165,962). Hoaglin and Hirsch [J.A.C.S., 71: 3468 (1949)] investigated this reaction further and broadened the possible applications, which Isler et al. likewise did in the 1950's, namely with respect to the synthesis of β-carotene, crocetin dialdehyde, lycopene as well as β-apocarotenoids [see Helv. Chim. Acta, 39: 249 et seq. and 463 et seq. (1956), ibid. 42: 854 et seq. (1959) as well as U.S. Pat. Nos. 2,827,481 and 2,827,482]. Later, Mukaiyama [Angew. Chem., 89: 858 et seq. (1977) and Org. Reactions, 28: 203 et seq. (1982)] extended the reaction by using the advantageous and readily accessible trimethylsilyl enol ethers.

The first Lewis acid-catalyzed condensations of 1-alkoxy-1,3-dienes (dienol ethers) with α,β-unsaturated acetals were reported by Nazarov and Krasnaya [J. Gen. Chem. USSR, 28: 2477 et seq. (1958)] and by Makin [Pure & Appl. Chem., 47: 173 et seq. (1976), J. Gen. Chem. USSR, 31: 3096 et seq. (1961) and 32: 3112 et seq. (1962)]. Here, the coupling of the acetal to the dienol ether takes place as far as can be seen exclusively at its γ-position with the formation of a chain-lengthened (α,β-unsaturated acetal, which, however, in competition with the first acetal reacts with further dienol ether with the formation of a further, chain-lengthened α,β-unsaturated acetal etc. [telomer formation; see also Chemla et al., Bull. Soc. Chim. Fr., 130: 200 et seq. (1993)]. For this reason such a condensation has been found not to be workable for synthetic purposes, especially for the synthesis of apocarotenoids [Isler et al., Adv. Org. Chem., 4: 115 et seq. (1963)].

Not only 1-alkoxy-1,3-dienes, but also trimethylsilyloxy-dienes [of the type $CH_2=CH-CH=CH-OSi(CH_3)_3$] can be condensted with α,β-unsaturated acetals in the presence of Lewis acid catalysts, as disclosed by Mukaiyama et al. in Chem. Lett. 1975, 319 et seq. In this coupling too the attack seems to take place exclusively at the terminal (γ-) carbon atom of the diene system to form "γ-products" [(see Mukaiyama et al., Bull. Chem. Soc. Jap 50: 1161 et seq. (1977) and Japanese Patent Publication (Kokai) 36,645/1977]. In contrast to the reaction with 1-alkoxy-1,3-dienes, from which an (α,β-unsaturated acetal is produced, the reaction of trimethylsilyloxydienes with acetals affords an aldehyde which cannot react further with the diene (no telomer formation). By using this method Mukaiyama et al. were able to synthesize vitamin A [see Kokai 36,645/1977, Chem. Lett. 1975, 1201 et seq. and Bull. Chem. Soc. Japan 51: 2077 et seq. (1978)] and workers from Rhône-Poulenc developed new routes to carotenoids and vitamin A (see DOS 2,701,489 and A.E.C. Société de Chimie Organique et Biologique No. 7824350).

The aforementioned Lewis acid-catalyzed condensation of a dienol ether with an α,β-unsaturated acetal based on the works of Nazarov and Krasnaya, Makin as well as Chemla et al. would be a very valuable access to apocarotenals and bis-apocarotenals if the yields of the desired primary product of the type . . . $CH=CH-CH(Oalkyl^1)-CH_2-CH=CH-CH(Oalkyl^1)(Oalkyl^2)$ could be increased and the telomer formation could be suppressed. Thus, the desired polyene aldehyde of the type . . . $CH=CH-CH=CH-CH=CH-CHO$ could be obtained from this primary product by hydrolysis of the acetal group $C(Oalkyl^1)(Oalkyl^2)$ and elimination of $alkyl^1OH$. In addition to the fact that in this reaction the formation of the double bond takes place under catalytic conditions, no phosphorus-, silicon- or sulphur-containing reagents are required.

The object of the present invention is to manufacture chain-lengthened polyene aldehydes or dialdehydes starting from polyene acetals or diacetals while avoiding as far as possible the aforementioned disadvantages of the state of the art and replacing the Wittig, Horner or Julia reaction hitherto used for this purpose.

SUMMARY OF THE INVENTION

The subject invention provides a process for manufacturing compounds of the formula:

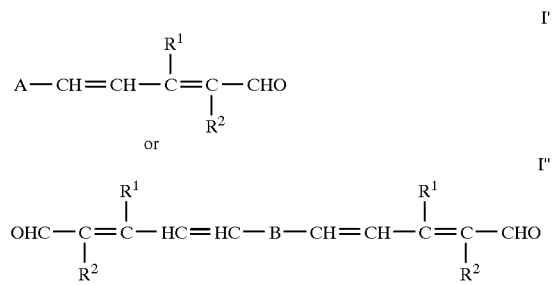

wherein

A is a monovalent conjugated polyene group or a methyl-substituted, monovalent conjugated polyene group, B is a bivalent conjugated polyene group or a methyl-substituted, bivalent conjugated polyene group and $R^1$ and $R^2$ each independently is hydrogen or methyl, with the $-CH=CH-C(R^1)=C(R^2)-CHO$ group(s) in each case being situated in the terminal position(s) of the conjugated chain of group A or B.

This process comprises:

(A) reacting a compound of formula:

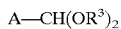    II' or

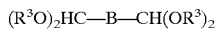    II"

wherein

A and B are as above, with the $-CH(OR^3)_2$ group(s) being situated in the terminal position(s) of the conjugated chain of group A or B, and $R^3$ is $C_{1-6}$-alkyl, with a compound of formula:

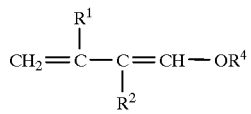
                                                                III wherein
  $R^1$ and $R^2$ are as above, and
  $R^4$ is $C_{1-6}$-alkyl,
in the presence of a Lewis acid or Brönsted acid to form an intermediate;

(B) hydrolyzing the intermediate to produce the compound of formula:

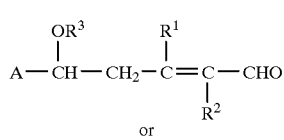
                                                                IV' or

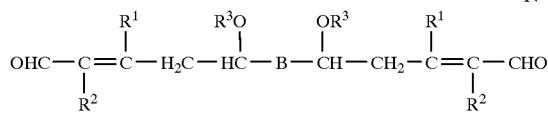
                                                                IV"

wherein
  A, B, $R^1$, $R^2$ and $R^3$ are as above, with the —CH(OR$^3$)—CH$_2$—C(R$^1$)=C(R$^2$)—CHO group(s) being situated in the terminal position(s) of the conjugated chain of group A or B; and (C) cleaving off the alcohol $R^3$OH from the compound of formula IV' or IV" under basic or acidic conditions.

The subject invention also provides compounds of formula:

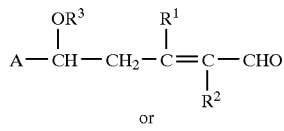
                                                                IV' or

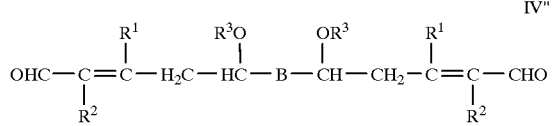
                                                                IV"

wherein
  A is a monovalent conjugated polyene group or a methyl-substituted, monovalent conjugated polyene group,
  B is a bivalent conjugated polyene group or a methyl-substituted, bivalent conjugated polyene group,
  $R^1$ and $R^2$ each independently is hydrogen or methyl, and
  $R^3$ is $C_{1-6}$-alkyl,
with the —CH(OR$_3$)—CH$_2$—C(R$^1$)=C(R$^2$)—CHO group(s) in each case being situated in the terminal position(s) of the conjugated chain of group A or B.

DETAILED DESCRIPTION OF THE INVENTION

The subject invention will now be described in terms of its preferred embodiments. These embodiments are set forth to aid in understanding the invention but are not to be construed as limiting.

The object of the invention is achieved by reacting a polyene O,O-dialkyl acetal or di(O,O-dialkyl acetal) with a 1-alkoxy-1,3-diene in the presence of a suitable catalyst, namely a Lewis acid or Brönsted acid, to give the corresponding chain-lengthened δ-alkoxy-α,β-unsaturated polyene aldehyde or di(δ-alkoxy-α,β-unsaturated) polyene dialdehyde in the form of its acetal or diacetal, hydrolyzing this di(acetal) to the corresponding di(aldehyde) and finally eliminating the δ-positioned alkanol from the thus-formed (di)aldehyde under basic or acidic conditions in order to obtain the desired (conjugated) polyene (di)aldehyde. Not only is the reaction of the 1-alkoxy-1,3-diene with the polyene O,O-dialkyl acetal or di(O,O-dialkyl acetal) novel, but surprisingly it takes place (so far as can be seen) with exclusive attack at the γ-position of the alkoxydiene. By base- or acid-induced elimination of the alkanol following the hydrolysis a (conjugated) C—C double bond is formed without requiring a phosphorus-, silicon- or sulphur-containing reagent, which is in contrast to the methodology hitherto usually used in this field.

Accordingly, the present invention is concerned with a process for the manufacture of a polyene aldehyde or polyene dialdehyde of formula

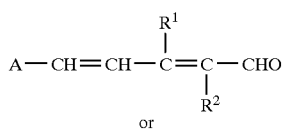
                                                                I' or

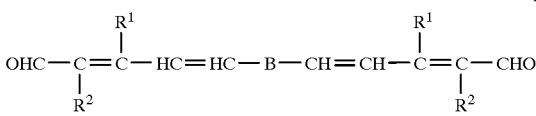
                                                                I"

wherein
  A signifies a monovalent, optionally methyl-substituted, conjugated polyene group,
  B signifies a bivalent, optionally methyl-substituted, conjugated polyene group and
  $R^1$ and $R^2$ each signify hydrogen or methyl,
    with the —CH=CH—C(R$^1$)=C(R$^2$)—CHO group(s) in each case being situated in the terminal position(s) of the conjugated chain of group A or B,
which process comprises reacting a polyene O,O-dialkyl acetal or di(O,O-dialkyl acetal) of formula

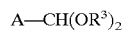
                                                                II' or

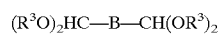
                                                                II"

wherein
  A and B have the significances given above, with in this case the —CH(OR$^3$)$_2$ group(s) being situated in the terminal position(s) of the conjugated chain of group A or B, and
  $R^3$ signifies $C_{1-6}$-alkyl, with a 1-alkoxy-1,3-diene of formula

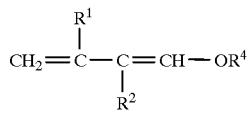

III wherein $R^1$ and $R^2$ have the significances given above and $R^4$ signifies $C_{1-6}$-alkyl, in the presence of a Lewis acid or Brönsted acid, hydrolyzing the reaction mixture and cleaving off the alcohol $R^3OH$ under basic or acidic conditions from the thus-produced compound of the formula

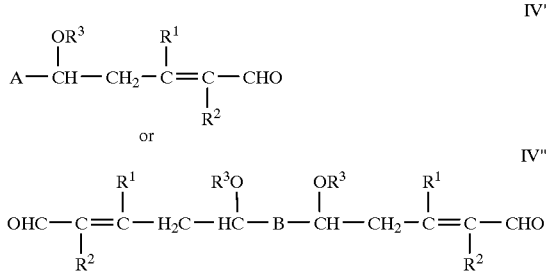

wherein

A, B, $R^1$, $R^2$ and $R^3$ have the significances given above, with in this case the —CH($OR^3$)—$CH_2$—C($R^1$)=C($R^2$)—CHO group(s) being situated in the terminal position(s) of the conjugated chain of group A or B.

The process in accordance with the invention can in principle be used in the case of all of the aforementioned polyene O,O-dialkyl acetals of formula II′ or polyene di(O,O-dialkyl acetals) of formula II″ which have the acetal group —CH($OR^3$)$_2$ at the end or at both ends of the polyene chain. Among such educts there are to be found, inter alia, the following sub-classes [with the abbreviated form of presentation which is usual in carotenoid chemistry (using simple lines) being used for the structural formulas]:

Alicyclic-aliphatic polyene O,O-dialkyl acetals, which mainly belong to the carotenoid field [as acetals of asymmetric carotenoid aldehydes having a six-membered (cyclohexene) ring], of the formula

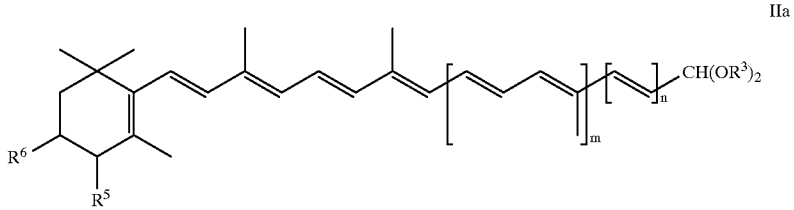

IIa wherein $R^3$ has the significance given above and $R^5$ and $R^6$ each independently signify hydrogen, an optionally protected hydroxy group or an optionally protected oxo group, m signifies 0, 1, 2, 3 or 4 and n signifies 0 or 1, which, after carrying out the multistage process in accordance with the invention, are converted into the corresponding alicyclic-aliphatic polyene aldehydes of the formula

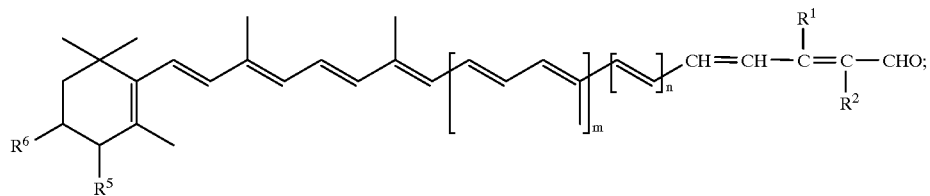

Ia aliphatic polyene O,O-dialkyl acetals, which likewise mainly belong to the carotenoid field (as acetals of open-chain asymmetric carotenoid aldehydes), of the formula

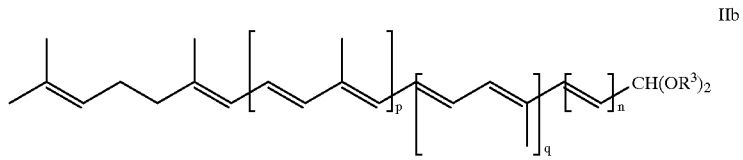

IIb wherein

R$^3$ has the significance given above and p signifies 0, 1 or 2, q signifies 0, 1, 2 or 3 and n signifies 0 or 1, which, after carrying out the multistage process in accordance with the invention, are converted into the corresponding aliphatic polyene aldehydes of the formula

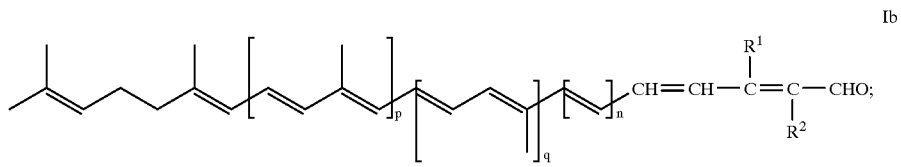

Ib aliphatic polyene di(O,O-dialkyl acetals), which likewise mainly belong to the carotenoid field (as acetals of symmetrical carotenoid dialdehydes), of the formula

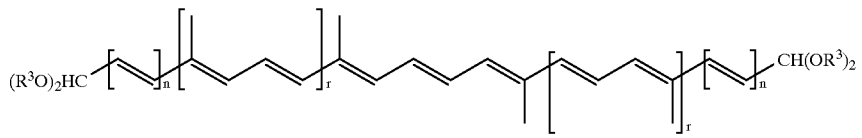

IIc wherein

R$^3$ has the significance given above and r signifies 0, 1 or 2 and n signifies 0 or 1, which, after carrying out the multistage process in accordance with the invention, are converted into the corresponding aliphatic polyene dialdehydes of the formula

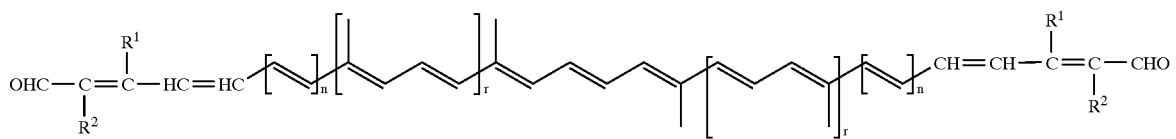

Ic

The educts of formulas IIa, IIb and IIc can be embraced by formula II:

$$R-CH(OR^3)_2 \qquad II$$

wherein

R signifies a group (a), (b) or (c)

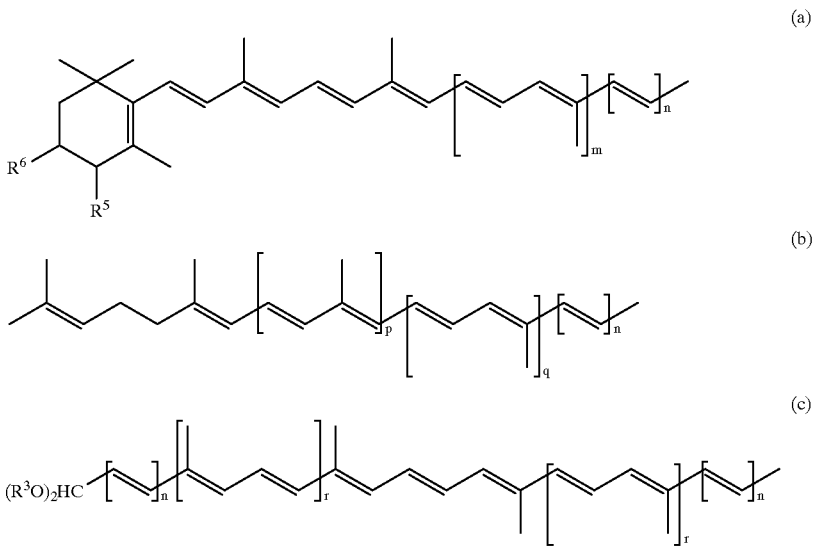

and $R^3$, $R^5$, $R^6$, m, n, p, q and r have the significances given above.

After carrying out the multistage process in accordance with the invention the educt of formula II is converted into the corresponding product of formula I:

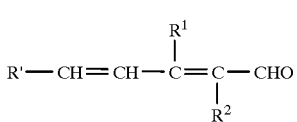

I wherein R' signifies a group (a) or (b) or a group (c')

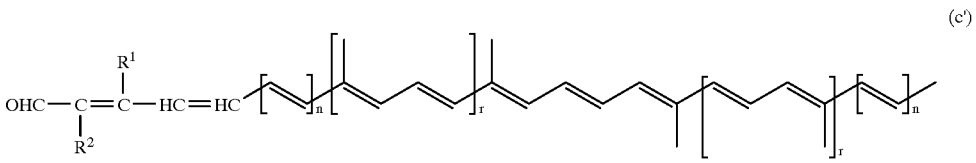

Formula I then embraces formulas Ia, Ib and Ic.

Where the product of formula I, especially of formula Ia, has one or two protected groups ($R^5$, $R^6$) on the cyclohexene ring, the protecting group(s) present can, if desired, be cleaved off, which represents a further aspect of the present invention.

In the scope of the present invention the term "$C_{1-6}$-alkyl" embraces straight-chain and branched groups such as, for example, methyl, ethyl and isobutyl.

The term "protected hydroxy group" embraces usual protected hydroxy groups (especially those which are familiar from the carotenoid field), particularly etherified hydroxy groups and acyloxy groups. The "etherified hydroxy groups" are, for example, $C_{1-5}$-alkoxy groups, preferably methoxy and ethoxy; $C_{2-16}$-alkoxyalkoxy groups, preferably 1-methoxy-1-methylethoxy; arylalkoxy groups, preferably benzyloxy; tetrahydropyranyloxy; and tri($C_{1-5}$-alkyl) silyloxy groups, preferably trimethylsilyloxy. The acyloxy groups embrace especially alkanoyloxy and aroyloxy groups with up to 8 carbon atoms such as, for example, formyloxy, acetoxy, propionyloxy and benzoyloxy.

The term "protected oxo group" also embraces usual protected oxo groups (especially those which are familiar from the carotenoid field). Acetalised oxo groups, especially those where the term protected oxo stands for two $C_{1-5}$-alkoxy groups (e.g. for two methoxy groups) or for a $C_{2-6}$-alkylenedioxy group (e.g. ethylenedioxy or 2,3-butylenedioxy, are preferred. Further, an oxo group can also be protected as an enol ether, primarily in the case of α-hydroxyketones (e.g. $R^5$ and $R^6$ signify hydroxy or oxo or vice versa), in which case the etherification of the enediol can preferably also be effected by the formation of a cyclic acetal or ketal (e.g. with acetone to the acetonide). The oxo group can also be protected, for example, as an imine.

The formulas of polyenes disclosed in the scope of the present invention embrace in each case isomeric forms, e.g. optically active and cis/trans or E/Z isomers, as well as mixtures thereof unless indicated to the contrary. The carbon atom carrying $R^5$ or $R^6$ where $R^5$ or $R^6$ signifies an optionally protected hydroxy group (see formulas Ia and IIa) can be mentioned as an example of a chiral (optically active) centre. With respect to E/Z isomerism, then there are generally preferred the (all-E) isomers of the educts and of the products of the process in accordance with the invention.

The first step of the process in accordance with the invention is conveniently carried out by reacting the polyene (di)O,O-dialkyl acetal of formula II' or II" with the 1-alkoxy-1,3-diene of formula III in an organic solvent at temperatures in the range of about −60° C. to about +60° C., preferably in the temperature range of about −20° C. to room temperature, and in the presence of a Lewis acid or Brönsted acid. Suitable organic solvents are, in general, all aprotic polar or non-polar solvents. Preferred among such solvents are lower aliphatic and cyclic hydrocarbons, e.g. n-pentane, n-hexane and cyclohexane; lower, halogenated aliphatic hydrocarbons, e.g. methylene chloride and chloroform; lower aliphatic and cyclic ethers, e.g. diethyl ether, tert.butyl methyl ether and tetrahydrofuran; lower aliphatic nitriles, e.g. acetonitrile; as well as aromatics, e.g. toluene. n-Hexane and toluene are especially preferred solvents. Examples of Lewis acids which can be used are zinc chloride, zinc bromide, titanium tetrachloride, lithium perchlorate, boron trifluoride etherate as well as iron(III) chloride; and examples of Brönsted acids which can be used are p-toluenesulphonic acid, methanesulphonic acid, trifluoromethanesulphonic acid, sulphuric acid as well as trifluoroacetic acid. These are generally used in catalytic amounts, conveniently in an amount of between about 0.5 and 5 mol percent based on the amount of polyene (di)O,O-dialkyl acetal employed and preferably in a mol percent range of 1% to 2%. Moreover, there are conveniently used about 1.05 to about 1.6 equivalents of 1-alkoxy-1,3-diene per equivalent of polyene O,O-dialkyl acetal or about 2.1 to about 3.2 equivalents of 1-alkoxy-1,3-diene per equivalent of polyene di(O,O-dialkyl acetal), preferably about 1.2 to about 1.4 and, respectively, about 2.4 to about 2.8 equivalents. Moreover, the reaction is conveniently effected at normal pressure, although in general the pressure is not critical.

If desired, the intermediate (the compound of formula IV' or IV" in the form of its dialkyl acetal) can be isolated from the reaction mixture and subsequently hydrolyzed to the corresponding compound of formula IV' or IV". However, it has been found to be convenient not to undertake such an isolation and subsequent hydrolysis, but to hydrolyze the intermediate in the reaction mixture itself immediately after completion of the reaction II'/II"+III in order to proceed to the compound of formula IV' or IV" (hereinafter abbreviated to IV'/IV") in these cases. The hydrolysis can be suitably effected by adding to the reaction mixture an aqueous solution of a weak acid, preferably slightly diluted aqueous acetic acid, and subsequently stirring the mixture for a time, for example about 30 minutes to about 2 hours, conveniently in the temperature range of about 0° C. to room temperature.

The respective product of formula IV' or IV" can be isolated from the reaction mixture and, if desired, purified in a manner known per se. Typically, the mixture is combined with water and the batch is extracted with a water-immiscible organic solvent such as, for example, with a lower alkane, dialkyl ether or aliphatic ester, e.g. n-hexane, tert.butyl methyl ether or ethyl acetate, and the organic phase is washed with water and/or saturated aqueous sodium chloride and/or sodium bicarbonate solution, dried and concentrated. An alternative involves adding water to the reaction mixture and filtering off the precipitated product which results from this, washing as in the case of the extract and then drying. The thus-isolated and at least to some extent washed crude product can then, if desired, be purified further, for example by column chromatography, e.g. using eluents such as n-hexane, ethyl acetate, toluene or mixtures thereof, or (re)crystallization, for example from an alcohol, e.g. methanol or ethanol. Alternatively, and often preferably, the crude product, taken up, for example, in a lower alkanol, can be reacted directly in the last process step of the present invention, i.e. in the sense of a "through process" II'/II"+ III→IV'/IV"→I'/I".

With respect to the last process step, i.e. the cleavage of the alcohol $R^3OH$ from the compound of formula IV' or IV", eliminations of alcohols from β-alkoxyaldehydes or δ-alkoxy-α,β-unsaturated aldehydes with the formation of the corresponding α,β- or α,β,γ,δ-unsaturated aldehydes are known in the scientific literature and can be carried out under a variety of conditions. For example, in the scope of known base-induced eliminations 1,8-diazabicyclo-[5.4.0] undec-7-ene is often used as the base in an amount of about 2 to 4 equivalents based on the amount of aldehyde used. Such conditions are used in the known manufacture of carotenoids [see, inter alia, Bull. Chem. Soc. Japan 50: 1161 et seq. (1977), ibid. 51: 2077 et seq. (1978), Chem. Lett. 1975, 1201 et seq. and German Offenlegungsschrift 2,701, 489] and of vitamin A (see, inter alia, Chem. Lett. 1975, 1201 et seq.). Aluminium oxide has also been used in the production of vitamin A by alcohol cleavage [J. Gen. Chem. USSR 32: 63 et seq. (1962)]. As examples of acid-induced alcohol cleavages reference is again made to Bull. Chem. Soc. Japan 50, 1161 et seq. (1977) and to J. Gen. Chem. USSR 30: 3875 et seq. (1960) in which p-toluenesulphonic acid and, respectively, 85% phosphoric acid are used as the acid catalyst. The buffer system sodium acetate/acetic acid [Helv. Chem. Acta. 39: 249 et seq. and 463 et seq. (1956) and U.S. Pat. Nos. 2,827,481 and 2,827,482] or sodium formate/formic acid [Synthesis 1981, 137 et seq.] has been used for such a cleavage, especially in the manufacture of carotenoids. Having regard to this and other relevant literature a person skilled in the art will be readily able to find suitable reaction conditions for the satisfactory performance of the last step of the process in accordance with the invention.

Furthermore, the cleavage of the alcohol $R^3OH$ can also be carried out using only catalytic amounts of a base, i.e. with less than one equivalent based on one equivalent of the compound of formula IV' or IV". Thus, the last process step in this case is conveniently carried out by converting the compound of formula IV' or IV", dissolved in a suitable organic solvent, in the presence of a catalytic amount of base with cleavage of the alcohol $R^3OH$ into the corresponding polyene (di)aldehyde of formula I' or I". Suitable organic solvents are generally protic, aprotic or mixtures thereof such as, for example, alcohols and mixtures of alcohols; or aromatics, e.g. toluene; and lower aliphatic esters, e.g. ethyl acetate. The base can be inorganic or organic, with strong bases such as, for example, alkali metal alcoholates, e.g. sodium methylate, sodium ethylate, potassium methylate, potassium ethylate and potassium tert.butylate; amines, e.g. triethylamine, 1,5-diazabicyclo[4.3.0]non-5-ene and 1,8-diazabicyclo[5.4.0]undec-7-ene; as well as alkali metal hydroxides and carbonates, especially sodium and potassium hydroxide or carbonate, being generally suitable. As mentioned above, a maximum of one equivalent of base is conveniently used per equivalent of compound of formula IV' or IV", preferably about 0.05 to about 0.3 equivalent. The reaction is suitably effected in the temperature range of about −20° C. to about 100° C., preferably at temperatures of about 0° C. to about 50° C. Moreover, the reaction is conveniently effected at normal pressure, although in general the pressure is not critical.

It has been found to be especially advantageous to carry out the last process step using a sodium alkoxide as the base and the corresponding alkanol as the solvent at temperatures between about −20° C. and the reflux temperature of the respective reaction mixture, preferably in a temperature range of about 0° C. to about 40° C. Conveniently, either a solution of the sodium alkoxide in the alcohol is prepared in advance or this solution is prepared freshly from metallic sodium and the alkanol. The bringing together of the alkanolic solution of the sodium alkoxide with the solution of the compound of formula IV'/IV" in the (same) alkanol, preferably likewise previously prepared, can be effected in any sequence and preferably at room temperature. Then, the reaction mixture is subsequently stirred for several hours and the reaction has normally finished at the latest after one to three hours.

Irrespective of the chosen procedure for the last process step, the product can be isolated from the reaction mixture and purified in a manner known per se. When a basic catalyst is used, the respective working-up normally comprises neutralization of the residual base by the addition of an organic or inorganic acid such as, for example, a carboxylic acid, e.g. acetic acid, or an aqueous mineral acid, e.g. dilute sulphuric acid.

In the particular embodiment of the procedure described above using a sodium alkoxide as the base, after completion of the reaction the mixture is conveniently cooled to room temperature or even to about 0° C. and thereafter preferably neutralized with aqueous acetic acid. The crystallization of the product of formula I' or I" can also be expedited by further cooling. After its isolation, suitably by filtration, the product can be washed, for example with water and/or aqueous alcohol, and finally dried, optionally under reduced pressure. If desired, further methods such as, for example, column chromatography and recrystallization can be employed in order to provide an even purer product.

If desired, protecting groups ($R^5$ and/or $R^6$ as a protected hydroxy or oxo group) which may be present in the obtained product of formula I' or I" can be cleaved off according to methods known per se, e.g. by hydrolysis with acid or base.

In the process in accordance with the invention defined above R preferably signifies either a group (a) in which $R^5$ and $R^6$ both signify hydrogen and n signifies 0, or a group (c) in which both n's signify 0, and in both cases $R^1$ and $R^2$ preferably signify hydrogen and methyl, respectively.

As mentioned above, in carrying out the process in accordance with the invention there is the advantage over the state of the art (especially the aforementioned works of Nazarov and Krasnaya, Makin as well as Chemla et al.) in that, inter alia, the telomer formation is largely suppressed. Although in the process in accordance with the invention the telomer formation resulting from the further reaction of the compound of formula IV' or IV" in acetal form with the 1-alkoxy-1,3-diene of formula III cannot always be suppressed completely, this is finally much less serious than expected. The cleavage of the alcohol $R^3OH$ from the compound of IV' or IV", occurring after the intermediate stage hydrolysis, can be effected readily in the presence of a telomer co-produced in a relatively small amount as a byproduct, e.g. of the formula A—CH($OR^3$)—$CH_2$—C($R^1$)=C($R^2$)—CH($OR^3$)—$CH_2$—C($R^1$)=C($R^2$)—CHO or OHC—($R^2$)C=($R^1$)C—$H_2$C—($R^3$O)HC—($R^2$)C=($R^1$)C—$H_2$C—($R^3$O)HC—B—CH($OR^3$)—$CH_2$—C($R^1$)=C($R^2$)—CH($OR^3$)—$CH_2$—C($R^1$)=C($R^2$)—CHO (in each case a single additional reaction), with an analogous alcohol cleavage from the telomer also taking place under the special reaction conditions which are used. However, the latter cleavage does not take place completely in that practically only the alcohol $R^3OH$ (δ-alkoxy) situated next to the terminal aldehyde group is cleaved off. The result of this incomplete alcohol cleavage from the telomer is that the desired product of formula I' or I" can be removed much more readily from the byproduct present at this stage than if all alkoxy groups $OR^3$ had been cleaved off from the telomer. Thus, the byproduct, which still has one or more substituents $OR^3$, remains in the mother liquor of the reaction mixture, while the desired product crystallizes out and is accordingly simple to remove, e.g. by filtration. It is wholly surprising that the telomer loses only the (respective) δ-positioned alcohol $R^3OH$ in the cleavage step of the process in accordance with the invention.

While some of the educts of the process in accordance with the invention are known, other precursors, which are in part known, can be produced according to methods known per se.

Thus, for example, the polyene O,O-dialkyl acetals of formula II' and the polyene di(O,O-dialkyl acetals) of formula II" can be produced very readily in a generally known manner by reacting the polyene monoaldehyde of the formula A—CHO or polyene dialdehyde of the formula OHC—B—CHO with the respective trialkyl orthoformate, especially in the corresponding $C_{1-6}$-alkanol, e.g. methanol for the O,O-dimethyl acetal, and in the presence of a catalytic amount of an organic acid or a Lewis acid, e.g. p-toluenesulphonic acid or zinc chloride, respectively (see, for example, Organikum, Organisch-chemisches Grundpraktikum, 6th edition, p. 377 et seq. (1963)]. The reaction takes place in suspension, i.e. the respective polyene monoaldehyde or dialdehyde is suspended in the alkanol and then conveniently about two or four mol equivalents, respectively, of the trialkyl orthoformate are added to the suspension, followed by a trace of acidic catalyst, e.g. p-toluenesulphonic acid. Thereby, the monoaldehyde or dialdehyde dissolves slowly and the formed polyene O,O-dialkyl acetal or di(O,O-dialkyl acetal) of formula II'/II" simultaneously crystallizes out slowly. The reaction is conveniently carried out in a temperature range of about 0° C. to about 40° C., and as a rule takes about 2 to about 4 hours. As further literature sources which illustrate the generally known acetalization method reference is made to European Patent Publications 252 389 and 391 033 as well as to J. Mol. Cat. 79: 117 et seq. (1993).

The polyene monoaldehydes A—CHO and dialdehydes OHC—B—CHO in turn are either known, especially from the technical literature concerning carotenoids, or—where novel—can be produced according to methods known per se. Thus, for example, the reaction of various $C_{15}$-Wittig salts with 2,7-dimethyl-2,4,6-octatrienedial (the so-called "$C_{10}$-dialdehyde") to give the corresponding monoaldehydes, the reaction of various $C_5$-Wittig aldehydes with long-chain polyene aldehydes likewise to give such monoaldehydes as well as the two-fold reaction of the $C_{10}$-dialdehyde with $C_5$- or $C_{10}$-Wittig aldehydes to give various dialdehydes are known from this literature. The textbook "Carotenoids" (O. Isler, published by Birkhäuser, Basel and Stuttgart, 1971), especially chapters VI and XII thereof and the further literature mentioned therein, provides much useful information relating to the production and the occurrence of the known monoaldehydes and dialdehydes. Where educts which have protected hydroxy, oxo or formyl groups are used, then such "protected" educts can be produced, for example, directly from the corresponding unprotected educts according to methods known per se.

The 1-alkoxy-1,3-dienes of formula III are in part known compound; the remaining (novel) compounds can be produced from known starting materials according to methods known per se.

Thus, for example, 1-ethoxy-2-methyl-1,3-butadiene (formula III in which $R^1$ signifies hydrogen, $R^2$ signifies methyl and $R^4$ signifies ethyl) has been known from the literature for a long time (see, inter alia, J.A.C.S. 91: 3281 et seq. (1969), Bull. Soc. Chim. Fr. 1963, 1646 et seq. as well as J. Gen. Chem. USSR 29: 3649 et seq. (1959)] and has in each case been produced by the two-fold cleavage of ethanol from 1,1,3-triethoxy-2-methyl-butane. The butane, in turn, can be produced by an enol ether condensation which has been known for a long time (see U.S. Pat. No. 2,165,962) from the two readily accessible starting materials acetaldehyde diethyl acetal and ethyl (1-propenyl) ether [see, moreover, J.A.C.S. 71: 3468 et seq. (1949) as well as J. Gen. Chem. USSR 29: 3641 et seq. (1959)]. Thereby, about 2 to 3 equivalents of the acetal per equivalent of ethyl propenyl ether are heated slightly at about 35° C. for up to about 2 hours with about 0.2 mol percent of boron trifluoride etherate as the catalyst in the absence of a solvent, with the desired butane being obtained in an about 66% yield. The subsequent two-fold cleavage of ethanol from the 1,1,3-triethoxy-2-methyl-butane has been realized in accordance with the relevant state of the art in two different ways:

(i) by cleavage in the liquid phase by adding the 1,1,3-triethoxy-2-methyl-butane dropwise to isoquinoline containing a catalytic amount of p-toluenesulphonic acid at about 220° C. and distilling off the 1-ethoxy-2-methyl-1,3-butadiene which is formed immediately. The yields are, however, moderate (about 40–50%) in this method which is described in Bull. Soc. Chim. Fr. 1963, 1646 et seq.; or (ii) by cleavage in the gas phase at 300–350° C. under a vacuum on an acidic catalyst, e.g. monosodium phosphate, magnesium dihydrogen phosphate or monoammonium phosphate [J. Gen. Chem. USSR 29: 3649 et seq. (1959)] or a basic catalyst, e.g. aluminium oxide (U.S. Pat. No. 2,573,678), with the yields lying in the range of about 50 to 80%.

A cleavage of ethanol in the gas phase at an elevated temperature on a fixed, solid catalyst is much more attractive for an industrial process than a cleavage in the liquid phase, since the former method has, inter alia, no solvent coupled with a simple reaction course and working up. Therefore, the cleavage carried out in the gas phase is preferred. The 1-methoxy-2-methyl-1,3-butadiene (formula III in which $R^1$ signifies hydrogen and $R^2$ and $R^4$ both signify methyl) is also known from the literature [Japanese Patent Publication (Kokai) 50891/1989]. It can be produced, for example, analogously to the production of 1-ethoxy-2-methyl-1,3-butadiene described above starting from acetaldehyde dimethyl acetal and methyl (1-propenyl) ether via 1,1,3-trimethoxy-2-methyl-butane.

Review articles for the production of 1-alkoxy-1,3-dienes will be found in Russian Chem. Rev. 38: 237 et seq. (1969) and in Pure and Appl. Chem. 47: 173 et seq. (1976); for additional literature concerning their production by gas phase catalysis reference is made to Lieb. Ann. Chem. 568: 1 et seq. (1950), Can. J. Res. B 28: 689 et seq. (1950), ibid. B 25: 118 et seq. (1947) as well as Chem. Ber. 77: 108 et seq. (1944).

The remaining 1-alkoxy-1,3-dienes of formula III are also in part known compounds and can be produced analogously to the aforementioned compounds. The following Reaction Scheme is a compilation of the multistage process illustrated in more detail above and in accordance with which all 1-alkoxy-1,3-dienes of formula III can be produced:

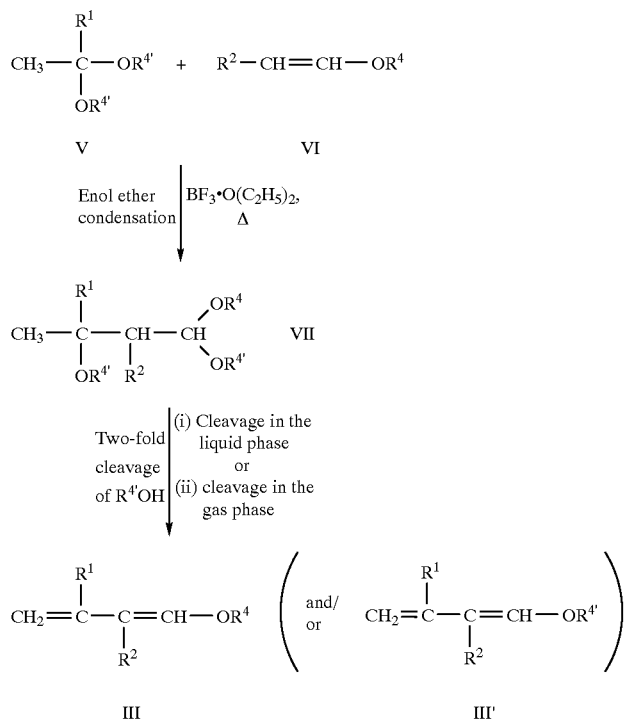

In this Reaction Scheme $R^1$, $R^2$ and $R^4$ have the significances given above; $R^{4'}$ signifies $C_{1-6}$-alkyl, conveniently—in order to avoid product mixtures—the same alkyl as $R^4$. Where $R^{4'}$ is different from $R^4$, a product mixture of the two compounds III and III' can thus result.

In the above-described production of the 1-alkoxy-1,3-dienes the respective product or intermediate can be isolated and purified in a manner known per se.

The intermediates of the process in accordance with the invention, i.e. the compounds of formulas IV' and IV", are novel compounds and represent a further aspect of the present invention.

Among these novel compounds of formulas IV' and IV" there are to be found:

15-Methoxy-15,15'-dihydro-12'-apo-β-carotenal,

12'-methoxy-11',12'-dihydro-8'-apo-β-carotenal,

8'-methoxy-7',8'-dihydro-4'-apo-β-carotenal,

4'-methoxy-β,ψ-caroten-16'-al, 11,12,11',12'-tetrahydro-12,12'-dimethoxy-8,8'-diapocarotene-8,8'-dial as well as 7,8,7',8'-tetrahydro-8,8'-dimethoxy-4,4'-diapocarotene-4,4'-dial.

The products of the process in accordance with the invention, i.e. the polyene aldehydes and dialdehydes of formulas I' and I", belong for the most part to the carotenoid field and can be used appropriately, for example as colorants or pigments for foodstuffs, egg yolk, the integuments (especially skin, legs and beak) and/or the subcutaneous fat of poultry, the flesh and/or the integuments (especially skin, scales and shell) of fish and crustaceans etc. This use can be effected according to methods known per se, as described, for example, in European Patent Publication No. 630,578.

The use of the novel products represents a further aspect of the present invention.

The invention is illustrated on the basis of the following Examples.

A. Production of polyene (di)O,O-dialkyl acetals (compounds of formulas II' and II")

EXAMPLE 1

15-Apo-β-carotenal dimethyl acetal (vitamin A aldehyde dimethyl acetal)

2.84 g (10 mmol) of vitamin A aldehyde (>99% pure) in 30 ml of methanol and 11 ml (100 mmol, 10 eq.) of trimethyl orthoformate were placed in a 100 ml four-necked sulphonation flask equipped with a magnetic stirrer, argon gasification and a thermometer. 40 mg (0.3 mmol, 3 mol %) of anhydrous zinc chloride were added thereto at 0° C. and the mixture was stirred at 0° C. for 3½ hours. Then it was cooled to −40° C. within one hour and filtered, and the solid was washed with a small amount of cold (at about −10° C.) methanol and finally dried. This gave 2.5 g (75% yield) of (all-E)-vitamin A aldehyde dimethyl acetal with m.p. 53–56° C.; content according to HPLC: 98.4%.

For analysis, a sample was recrystallized from methanol. This sample showed the following physical and analytical data: m.p. 53–55° C.; content according to HPLC: 99.7%; UV (n-hexane): 324 nm (log ε=4.70; $E_{1\ cm}^{1\%}$=1520).

Microanalysis: Calc.: C 79.95% H 10.37% Found: C 79.66% H 10.50%.

EXAMPLE 2

12'-Apo-β-carotenal dimethyl acetal 50 g (0.14 mol) of 12'-apo-β-carotenal and 31 ml (=30.1 g, 0.28 mol) of freshly distilled trimethyl orthoformate in 500 ml of methanol were placed in a 1.5 l four-necked sulphonation flask equipped with a mechanical stirrer, argon gasification and a thermometer. A solution of 16 mg of p-toluenesulphonic acid monohydrate in 4 ml of methanol was then added at room temperature to the resulting suspension. Thereby, the red crystals dissolved for the most part within 20 minutes; subsequently an orange precipitate began to form. After stirring at room temperature for 2 hours the mixture was cooled to about +5° C., 0.5 ml of triethylamine was added, the mixture was stirred at 0° C. for 15 minutes, suction filtered (pressure suction filter, under argon), and the solid washed with a small amount of cold (−10° C.) methanol and dried at room temperature for about 16 hours under reduced pressure (water-jet vacuum). This gave 52.3 g (90.5% yield) of 12'-apo-β-carotenal dimethyl acetal as an orange powder with m.p. 77–78° C.; content according to HPLC: 97.5% (very acid-labile); UV (n-hexane): 393 nm (log ε=4.91; $E_{1\ cm}^{1\%}$=2045), 376 nm (log ε=4.91; $E_{1\ cm}^{1\%}$=2045).

Microanalysis: Calc.: C 81.77% H 10.17% Found: C 81.50% H 9.84%.

EXAMPLE 3

8'-Apo-β-carotenal dimethyl acetal 6.25 g (15 mmol) of 8'-apo-β-carotenal and 6.6 ml (=6.4 g, 60 mmol, 4 eq.) of trimethyl orthoformate in 200 ml of methanol were placed in a 350 ml four-necked sulphonation flask equipped with a mechanical stirrer, argon gasification and a thermometer. A solution of 20 mg of p-toluenesulphonic acid monohydrate in 10 ml of methanol was added thereto at room temperature and the mixture was stirred for 2½ hours. Thereby, the red crystals dissolved slowly and an orange crystallizate began to form. Then 2 ml of triethylamine were added, the mixture was cooled to 0° C. within about 30 minutes and suction filtered, and the solid was washed with a small amount of cold (−10° C.) methanol and dried briefly under reduced pressure (water-jet vacuum). After 30 minutes this gave 11.6 g of methanol-moist acetal with a content of 94.8% according to HPLC. For recrystallization, the crystals were dissolved in 200 ml of diethyl ether and then 600 ml of methanol were added thereto within 1½ hours, the mixture was cooled to 0° C. and the crystals were filtered off and dried at room temperature under reduced pressure (water-jet vacuum) and briefly under a high vacuum. This gave 5.9 g (84% yield) of 8'-apo-β-carotenal dimethyl acetal as rust-red crystals with m.p. 131–132° C.; content according to HPLC: 98.4%; UV (n-hexane): 450 nm (log ε=5.06; $E_{1\ cm}^{1\%}$=2476), 424 nm (log ε=5.07; $E_{1\ cm}^{1\%}$=2543).

Microanalysis: Calc.: C 83.06% H 10.02% Found: C 82.91% H 10.13%.

EXAMPLE 4

4'-Apo-β-carotenal dimethyl acetal 10 g (20.7 mmol) 4'-apo-β-carotenal and 35 ml (0.31 mol, about 15 eq.) of trimethyl orthoformate in 250 ml of methanol were placed in a 500 ml four-necked sulphonation flask equipped with a mechanical stirrer, argon gasification and a thermometer. A solution of 25 mg of p-toluenesulphonic acid monohydrate in 15 ml of methanol was added at room temperature to the resulting dark red suspension, the mixture was stirred at room temperature for 45 minutes and then at 30–35° C. for 1½ hours; the dark red suspension changed to a brown suspension. Subsequently, 2 ml of triethylamine were added and the mixture was cooled to 0° C. The precipitated crude product was filtered off under suction, washed with a small amount of cold methanol and dried briefly at room temperature under reduced pressure. The thus-obtained methanol-moist product (about 17.8 g; content according to HPLC: 91%) was dissolved in 600 ml of diethyl ether with slight warming and treated at room temperature within 1 hour with 1 l of methanol (containing 2% triethylamine). Then the mixture was suction filtered and the residue was washed with a small amount of cold (0° C.)

methanol. This gave, after drying at room temperature and under reduced pressure for 2 hours, 9.3 g (80.5% yield) of 4'-apo-β-carotenal dimethyl acetal as violet crystals with a content of 94.7% according to HPLC.

In order to obtain the analytical data, a sample was recrystallized from diethyl ether (dissolved while warming and cooled to 0° C.): content according to HPLC: 95.7%; m.p. 186–188° C.; UV (dioxan): 500 nm (log ε=4.93; $E\backslash o(_{1\ cm}^{1\%})$=1623), 468 nm (log ε=4.99; $E_{1\ cm}^{1\%}$=1837), 283 nm (log ε=4.37; $E_{1\ cm}^{1\%}$=444).

EXAMPLE 5
12,12'-Diapoarotenal dimethyl acetal ($C_{10}$-dialdehyde dimethyl acetal)

32.8 g (0.2 mol) of $C_{10}$-dialdehyde and 65 g of trimethyl orthoformate in 250 ml of methanol were placed in a 500 ml round flask equipped with a magnetic stirrer and argon gasification. 100 mg of p-toluenesulphonic acid monohydrate were added thereto at about 20° C., which produced a slightly exothermic reaction. The reaction mixture was held at about 20–25° C. using a cold water bath. The suspension dissolved in about 5 minutes. Then the mixture was stirred at room temperature for one hour and about 0.5 ml of triethylamine was subsequently added. The mixture was concentrated under reduced pressure and the separated crystal slurry was dissolved in 200 ml of hot n-hexane, filtered while hot through cotton wool and left to stand. The solution was left to stand at −20° C. in a deep freezer for about 16 hours and the resulting crystals were filtered off, washed with n-hexane at −20° C. and dried to constant weight under a water-jet vacuum. This gave 42.7 g (80% yield) of $C_{10}$-dialdehyde dimethyl acetal as pale yellow crystals with m.p. 68–69° C. and a content according to gas chromatography (GC) of about 96%); UV (ethanol): 292 nm (log ε=4.61; $E_{1\ cm}^{1\%}$=1602), 280 nm (log ε=4.72; $E_{1\ cm}^{1\%}$=2046), 260 nm (log ε=4.59; $E_{1\ cm}^{1\%}$=1508).

Microanalysis: Calc.: C 65.60% H 9.44% Found: C 65.43% H 9.14%.

EXAMPLE 6
8,8'-Diapocarotenal dimethyl acetal (crocetin dialdehyde dimethyl acetal)

20.0 g (67.5 mmol) of crocetin dialdehyde (m.p. 196–197° C.) and 40 g (0.37 mol) of trimethyl orthoformate in 350 ml of methanol were placed in a 500 ml round flask equipped with a magnetic stirrer and argon gasification. 200 mg of p-toluenesulphonic acid monohydrate were added thereto at room temperature while stirring and the mixture was stirred at room temperature for about 45 minutes and at 35–40° C. for about 1½ hours, which gave a yellow-orange suspension. Then the mixture was cooled to 0° C., filtered and the residue was washed with cold methanol (−10° C.). This gave 24.7 g (92% yield) of crocetin dialdehyde dimethyl acetal as an orange powder, m.p. 136° C., with a content of 97.4% according to HPLC. Recrystallization from 150 ml of hot ethyl acetate and 150 ml of methanol while cooling to −20° C. gave, after filtration and drying (water-jet vacuum, followed by high vacuum), 23.3 g (86% yield) of crocetin dialdehyde dimethyl acetal as rust-red, crystals, m.p. 138–139° C., with a content of 97.3% according to HPLC; UV (ethanol): 422 nm (log ε=5.12; $E_{1\ cm}^{1\%}$=3416), 397 nm (log ε=5.11; $E_{1\ cm}^{1\%}$=3305), 377 nm (log ε=4.89; $E_{1\ cm}^{1\%}$=1985), 232 nm (log ε=4.20; $E_{1\ cm}^{1\%}$=405).

Microanalysis: Calc.: C 74.19% H 9.34% Found: C 74.10% H 9.47%.

B. Production of the compounds of formulas IV' and IV" from the polyene (di)O,O-dialkyl acetals of formula II' and II", respectively, and the 1-alkoxy-1,3-dienes of formula III

EXAMPLE 7
15-Methoxy-15,15'-dihydro-12'-apo-β-carotenal 2.38 g (7 mmol) of vitamin A aldehyde dimethyl acetal (HPLC: 97.8%) and 1.13 g (11.2 mmol) of 1-methoxy-2-methyl-1,3-butadiene (GC: 98%) in 50 ml of toluene were placed under argon in a two-necked round flask equipped with a magnetic stirrer and a thermometer. The mixture was cooled to −20° C., 15 mg (1 mol %) of p-toluenesulphonic acid monohydrate were added thereto and the mixture was stirred at −20° C. for 2 hours. In order to establish the course of the reaction, a sample was then removed and hydrolyzed with 1 to 2 drops of 90% aqueous acetic acid; the mixture was diluted with a large amount of water, the aqueous solution was extracted with a small amount of toluene and the extract was investigated by thin-layer chromatography [tlc; on silica gel ($SiO_2$)], with the following result: tlc ($SiO_2$): $R_f$=about 0.3; toluene/ethyl acetate (19:1).

For the hydrolysis, 10 ml of acetic acid/water (9:1) were added to the content of the round flask and the mixture was stirred at 0° C. for one hour. For the working up, the mixture was poured into 35 ml of water and extracted twice with 35 ml each time, a total of 70 ml, of ethyl acetate. Then the combined organic phases were washed three times with 35 ml each time, a total of 105 ml, of water, once with saturated sodium bicarbonate solution and once with saturated sodium chloride solution, dried over anhydrous sodium sulphate, filtered and concentrated under reduced pressure. This gave 3.0 g of yellow, oily crude product which was chromatographed on 300 g of silica gel (0.04–0.063 mm) with toluene/ethyl acetate (19:1 to 9:1). This gave 1.2 g (40% yield) of (all-E)-15-methoxy-15,15'-dihydro-12'-apo-β-carotenal with a content according to HPLC of 90.5%; UV (cyclohexane, 2% chloroform): 328 nm (log ε=4.59; $E_{1\ cm}^{1\%}$=1007). A material purified further by chromatography and having a content of 94.8% according to HPLC was used for the spectroscopic characterization: IR (film): 1690 $cm^{-1}$ (CHO); mass spectrum: 382 ($M^+$, 55), 299 (100).

About 13% of oily (13Z)-15-methoxy-15,15'-dihydro-12'-apo-β-carotenal was isolated as a byproduct. A sample with a content of 95.4% according to HPLC was used for the characterization of this byproduct: $^1$H-NMR ($CDCl_3$, 250 MHz): 9.46 ppm (CHO); IR (film): 1689 $cm^{-1}$ (CHO); mass spectrum: 382 ($M^+$, 50), 299 (100).

EXAMPLE 8
12'-Methoxy-11',12'-dihydro-8'-apo-β-carotenal 1.98 g (5 mmol) of 12'-apo-β-carotenal dimethyl acetal (HPLC: about 98%) and 0.78 g (8 mmol) of 1-methoxy-2-methyl-1,3-butadiene (GC: 96%) in 40 ml of n-hexane were placed in a 100 ml two-necked round flask equipped with a magnetic stirrer and a thermometer. 34 mg (3.5 mol %) of p-toluenesulphonic acid monohydrate were added thereto at −25° C. and the mixture was stirred at −25° C. for 2 hours [tlc ($SiO_2$) after prior hydrolysis: $R_f$=about 0.3; toluene/ethyl acetate (19:1)].

For the hydrolysis, 10 ml of acetic acid/water (9:1) were then added to the contents of the round flask and the mixture was stirred at 0° C. for 30 minutes. For the working up, the mixture was poured into 25 ml of water and extracted twice with 25 ml each time, a total of 50 ml, of ethyl acetate. Then the combined organic phases were washed three times with 25 ml each time, a total of 75 ml, of water, once with saturated sodium bicarbonate solution and once with saturated sodium chloride solution, dried over anhydrous sodium sulphate, filtered and concentrated under reduced pressure. This gave 2.9 g of oily, red crude product which was chromatographed on 70 g of silica gel (0.04–0.063 mm) with toluene/ethyl acetate (19:1). There were obtained 2.01 g (86% yield) of 12'-methoxy-11',12'-dihydro-8'-apo-β-carotenal as an orange oil with a content of 96.2% according to HPLC. The spectroscopic data were obtained from a different batch (content according to HPLC: 96%): UV (n-hexane): 395 nm (log ε=4.89; $E_{1\ cm}^{1\%}$=1752), 377 nm (log ε=4.91; $E_{1\ cm}^{1\%}$=1794); $^1$H-NMR (400 MHz, CDCl$_3$): 9.40 ppm (C$\underline{H}$O), 3.22 ppm (OC$\underline{H}_3$); IR (film): 1688 cm$^{-1}$ (CHO); mass spectrum: 448 (M$^+$, 75), 365 (100).

EXAMPLE 9
8'-Methoxy-7',8'-dihydro-4'-apo-β-carotenal 2.36 g (5 mmol) of 8'-apo-β-carotenal dimethyl acetal (content according to HPLC: 98%) and 0.82 g (8 mmol, 1.6 eq.) of 1-methoxy-2-methyl-1,3-butadiene (GC: 96%) in 50 ml of toluene were placed under argon in a 100 ml two-necked round flask equipped with a magnetic stirrer and a thermometer. 30 mg (0.16 mmol, 3 mol %) of p-toluenesulphonic acid monohydrate were added at −15° C. and the mixture was stirred at −15° C. for one hour [tlc (SiO$_2$) after prior hydrolysis: R$_f$=about 0.3; toluene/ethyl acetate (19:1)].

For the hydrolysis, 10 ml of acetic acid/water (9:1) were then added at −15° C., the mixture was stirred for 1½ hours at 0° C. and worked up analogously to Example 7 or 8. This gave 3.2 g of crude 8'-methoxy-7',8'-dihydro-4'-apo-β-carotenal [HPLC ratio product:byproduct (telomer)= 98.5:1.5) as a red, viscous residue. This was digested in 50 ml of methanol at 45° C. for 45 minutes, then filtered off under suction, washed with cold (0° C.) methanol and dried under a high vacuum, which gave 1.96 g (73% yield) of 8'-methoxy-7',8'-dihydro-4'-apo-β-carotenal as orange-red crystals with m.p. 152–153° C. [HPLC ratio product:byproduct=95.8:1.4].

For analysis, a sample (300 mg) was recrystallized from hot ethanol. This gave 155 mg of pure 8'-methoxy-7',8'-dihydro-4'-apo-β-carotenal with m.p. 158–159° C.; content according to HPLC: 100%; UV (cyclohexane with 3% chloroform): 456 nm (log ε=5.03; $E_{1\ cm}^{1\%}$=2105), 430 nm (log ε=5.08; $E_{1\ cm}^{1\%}$=2335); $^1$H-NMR (400 MHz, CDCl$_3$): 9.40 ppm (C$\underline{H}$O), 3.22 ppm (OC$\underline{H}_3$); IR (KBr): 1680 cm$^{-1}$ (CHO); mass spectrum: 514 (M$^+$, 100), 431 (25); microanalysis: Calc.: C 83.99% H 9.79% Found: C 83.69% H 10.03%.

EXAMPLE 10
4'-Methoxy-β,ψ-caroten-16'-al 2.32 g (4.25 mmol) of 4'-apo-β-carotenal dimethyl acetal (content according to HPLC: 97%) and 0.682 g (6.8 mmol, 1.6 eq.) of 1-methoxy-2-methyl-1,3-butadiene (GC: 98%) in 40 ml of toluene were placed under argon in a 25 ml two-necked round flask. 25 mg (0.13 mmol, 3 mol %) of p-toluenesulphonic acid monohydrate were added at −25° C. and the mixture was stirred at this temperature for 3½ hours [tlc (SiO$_2$) after prior hydrolysis: R$_f$=about 0.3; toluene/ethyl acetate (19:1)].

Then, for the hydrolysis, 20 ml of acetic acid/water (9:1) were added thereto and the mixture was stirred at 0° C. for one hour. An extractive working up as described in Example 7 or 8 gave 4.2 g of crude product which was chromatographed on 400 g of silica gel (0.04–0.063 mm) with toluene/ethyl acetate (19:1). There were obtained 2.43 g of a red solid with m.p. 148–154° C. which was digested by stirring in 25 ml of ethanol at 50° C. for one hour. Subsequently, the mixture was cooled to 0° C., filtered and washed with a small amount of ethanol. After drying under a high vacuum there were obtained 1.36 g (54% yield) of 4'-methoxy-β,ψ-caroten-16'-al as red-brown crystals which m.p. 158–160° C.; content according to HPLC: 97.1%.

An analytical sample with m.p. 161–163° C. was used for the analysis: UV (cyclohexane/3% chloroform): 497 nm (log ε=5.13;

$E_{1\ cm}^{1\%}$=1986), 465 nm (log ε=5.19; $E_{1\ cm}^{1\%}$=2258), 440 nm (log ε=5.02; $E_{1\ cm}^{1\%}$=1550), 283 nm (log ε=4.48; $E_{1\ cm}^{1\%}$=443); $^1$H-NMR (250 MHz, CDCl$_3$): 9.40 ppm (C$\underline{H}$O); IR (KBr): 1688 cm$^{-1}$ (CHO); mass spectrum: 580 (M$^+$/4), 118 (100).

Microanalysis: Calc.: C 84.77% H 9.72% Found: C 84.55% H 9.42%.

EXAMPLE 11
11,12,11',12'-Tetrahydro-12,12'-dimethoxy-8,8'-diapocarotene-8,8'-dial 10.30 g (40 mmol) of C$_{10}$-dialdehyde dimethyl acetal (HPLC: 99.6%) were placed in 200 ml of toluene under argon in a 350 ml four-necked sulphonation flask equipped with a magnetic stirrer, a dropping funnel and a thermometer. The solution was cooled to −25° C. and there were added thereto while stirring 76 mg (0.4 mmol, 1 mol %) of p-toluenesulphonic acid, followed by a solution of 9.1 g (90 mmol, 2.25 eq.) of 1-methoxy-2-methyl-1,3-butadiene in 16 ml of toluene. The addition of this solution took about 10 minutes, during which the temperature was held in the range of about −20° C. to −25° C. The mixture was stirred at −20° C. for a further hour [tlc (SiO$_2$) after prior hydrolysis: R$_f$=about 0.3 (product) and about 0.5 (acetal); toluene/ethyl acetate (4:1)].

Then, for the hydrolysis, 20 ml of acetic acid/water (9:1) were added to the contents of the flask, and the mixture was stirred at room temperature for 1 hour. An extractive working up as described in Example 7 or 8 gave, after two-fold chromatography on 500 g of silica gel (0.04–0.063 mm) with toluene/ethyl acetate (9:1) and a single chromatography on 700 g of silica gel (0.04–0.063 mm) with cyclohexane/ ethyl acetate (3:1), 10.0 g (67% yield according to HPLC) of yellow, in part solid 11,12,11',12'-tetrahydro-12,12'-dimethoxy-8,8'-diapocarotene-8,8'-dial with a content of the desired product of 97.1% according to HPLC. By crystallization of this crude product from ethanol there could be obtained a purer product, m.p. 105–107° C., which gave the following analysis: UV (cyclohexane/5% chloroform): 300 nm (log ε=4.57), 287 nm (log ε=4.69); IR (KBr): 1679 cm$^{-1}$ (CHO); mass spectrum: 360 (M$^+$, 1), 194 (100).

EXAMPLE 12
7,8,7',8'-Tetrahydro-8,8'-dimethoxy-4,4'-diapocarotene-4,4'-dial 4.04 g (10 mmol) of crocetin dialdehyde dimethyl acetal (HPLC: 96.2%) in 50 ml of ethyl acetate were placed under argon in a 200 ml four-necked flask. At −15° C. there were added thereto while stirring 38 mg (2 mol %) of p-toluenesulphonic acid, followed by a solution of 2.82 g (28 mmol 2.8 eq.) of 1-methoxy-2-methyl-1,3-butadiene in 4 ml of ethyl acetate. The mixture was stirred at −15° C. for 3 hours [tlc (SiO$_2$) after prior hydrolysis: R$_f$=about 0.3 (product) and about 0.5 (acetal); toluene/ethyl acetate (9:1)].

Then, for the hydrolysis, 10 ml of acetic acid/water (9:1) were added to the contents of the flask and the mixture was stirred at room temperature for 2 hours. An extractive working up as described in Example 7 or 8 gave, after chromatography on 500 g of silica gel (0.04–0.063 mm) with methylene chloride/ethyl acetate (19:1), 2.4 g (43% yield according to HPLC) of 7,8,7',8'-tetrahydro-8,8'-dimethoxy-4,4'-diapocarotene-4,4'-dial as an orange powder (content of desired product according to HPLC 89%).

A sample with m.p. 179–187° C. (isomer mixture) and 91.7% purity according to HPLC, chromatographed again and recrystallized from methylene chloride/ethanol, was used for the analysis: UV (cyclohexane/2% chloroform): 428 nm (log $\epsilon$=5.14), 402 nm (log $\epsilon$=5.12), 381 nm (log e =4.90); IR (KBr): 1679 cm$^{-1}$ (CHO); mass spectrum: 492 (M$^+$, 100).

C. Manufacture of the polyene(di)aldehydes of formulas I' and I" from the compounds of formula IV' and IV", respectively

EXAMPLE 13

12'-Apo-β-carotenal 1.20 g (2.82 mmol) of (all-E)-15-methoxy-15,15'-dihydro-12'-apo-β-carotenal (content according to HPLC: 90%) in 7 ml of ethanol were placed in a 10 ml round flask and treated with 0.11 ml (0.6 mmol, 20 mol %) of a 5.4M sodium methylate solution in methanol. The mixture was stirred at room temperature for one hour [tlc (SiO$_2$): R$_f$=about 0.5; toluene/ethyl acetate (19:1)].

For the neutralization, 5 drops of acetic acid were added to the resulting deep red suspension and the mixture was then cooled to 0° C. for one hour, filtered and the resulting crystals were washed with a small amount of ice-cold methanol and water and dried under a high vacuum at room temperature to constant weight. This gave 0.76 g (75% yield) of 12'-apo-β-carotenal as deep red crystals with m.p. 107–109° C.; content according to HPLC: 98.1%. UV (cyclohexane, 2% chloroform): 4.17 nm (log $\epsilon$=4.87; $E_{1\,cm}^{1\%}$=2114); $^1$H-NMR (250 MHz,CDCl$_3$): 9.45 ppm (CHO); IR (KBr): 1663 cm$^{-1}$ (CHO); mass spectrum: 350 (M$^+$, 100).

Microanalyse: Calc.: C 85.66% H 9.78% Found: C 85.45% H 9.49%.

EXAMPLE 14

8'-Apo-β-carotenal (through process from 12'-apo-β-carotenal dimethyl acetal and 1-methoxy-2-methyl-1,3-butadiene via 12'-methoxy-11',12'-dihydro-8'-apo-β-carotenal 8.02 g (20 mmol) of 12'-apo-β-carotenal dimethyl acetal (content according to HPLC: about 99%) and 2.96 g (29 mmol) of 1-methoxy-2-methyl-1,3-butadiene (GC: about 96%) in 150 ml of n-hexane were placed under argon in a 200 ml sulphonation flask equipped with a magnetic stirrer and a thermometer. 40 mg (0.21 mmol, 1 mol %) of p-toluenesulphonic acid monohydrate were added at –25° C. and the mixture was stirred at –22 to –25° C. for 2 ½ hours. (The 12'-apo-β-carotenal dimethyl acetal is soluble at room temperature, but again precipitates at –25° C.). During the reaction the resulting pale yellow suspension dissolved slowly with the formation of a dark green solution which became brownish in colour at the end of the reaction [tlc (SiO$_2$) after prior hydrolysis: R$_f$ of the product=about 0.4; R$_f$ of the starting material (acetal)=about 0.5; toluene/ethyl acetate (19:1)].

For the hydrolysis, 20 ml of acetic acid/water (9:1) were then added at –25° C. and the reaction solution was stirred at 0° C. for one hour.

For the working up, the mixture was poured into 100 ml of water and extracted with 100 ml each time, a total of 200 ml, of n-hexane. Subsequently, the organic phase was washed in sequence with water, with 100 ml of saturated sodium bicarbonate solution and with 100 ml of saturated sodium chloride solution. Then, the organic phase was dried over anhydrous sodium sulphate, filtered and concentrated under reduced pressure. About 80 ml of ethanol were added to the resulting residue and the solution was again concentrated in order to remove residues of hexane. This gave 10.6 g of crude, still ethanol-moist 12'-methoxy-11',12'-dihydro-8'-apo-β-carotenal as a red-orange, viscous oil [HPLC: 86.4% product, 5% byproduct (telomer); ratio product:byproduct=94.5:5.5]. This oil was now dissolved in 170 ml of ethanol and transferred under argon into a 250 ml round flask equipped with a magnetic stirrer. 0.4 ml (about 2 mmol, 10 mol %) of a 5.4M solution of sodium methylate in methanol was added to the red-orange solution at room temperature while stirring. In so doing, the reaction solution immediately became deep dark red in colour and crystallization began after about 5 to 10 minutes. The mixture was stirred at room temperature for about 1 hour [tlc (SiO$_2$): R$_f$ (intermediate)=about 0.4, R$_f$ (product)=about 0.7; toluene/ethyl acetate (19:1)].

Then the mixture was cooled (about ½ hour) at 0° C. with an ice bath and neutralized with 0.5 g (about 8 mmol) of acetic acid in 2–3 ml of ethanol. 3.5 ml of water were added dropwise and the mixture was left to stand at +5° C. (refrigerator) for about 16 hours. Thereafter, the precipitate was filtered off with a glass suction filter and washed twice with 20 ml each time, a total of 40 ml, of ethanol/water (19:1) at 0° C., then with 70 ml of water at room temperature and twice more with 10 ml each time, a total of 20 ml, of ethanol/water (19:1) at 0° C. After drying under a water-jet vacuum at 45° C. and under a high vacuum at room temperature there were obtained 7.53 g (83% yield) of 8'-apo-β-carotenal as a blue, crystalline powder with m.p. 137–138° C. and a content of 92% according to HPLC.

For further purification, 7.48 g of the above powder were dissolved in 110 ml of acetone under reflux for about 10 minutes. The solution was then treated dropwise through the condenser under reflux and while stirring vigorously with 8 ml of water, which triggered off a crystallization, and the mixture was then cooled slowly to 0° C. After stirring in an ice bath for about 2 hours the precipitate was filtered off and washed twice with 30 ml each time, a total of 60 ml, of ethanol/water (9:1) at 0° C., twice with 30 ml each time, a total of 60 ml, of water and finally three times with 5 ml each time, a total of 15 ml, of ethanol/water (9:1) at 0° C. After drying under a water-jet vacuum at 45° C. and under a high vacuum at room temperature there were obtained 6.79 g (81% yield) of pure 8'-apo-β-carotenal as violet crystals with m.p. 141–142° C. and a content of 99.5% according to HPLC.

The analytical data were obtained using an analogous batch: m.p. 141–143° C.; content according to HPLC: 95.4%; UV (cyclohexane with 3% chloroform): 460 nm (log $\epsilon$=5.03, $E_{1\,cm}^{1\%}$=2562); $^1$H-NMR (400 MHz, CDCl$_3$): 9.45 ppm (CHO); IR (KBr): 1669, 1609 cm$^{-1}$; mass spectrum: 416 (M$^+$, 100); microanalysis: Calc.: C 86.48% H 9.68% Found.: C 86.23% H 9.54%.

EXAMPLE 15

4'-Apo-β-carotenal 1.96 g (3.65 mmol) of 8'-methoxy-7',8'-dihydro-4'-apocarotenal (content according to HPLC: 95.7%) in 50 ml of ethyl acetate/methanol (1:1) were placed under argon in a 100 ml round flask equipped with a magnetic stirrer. 0.1 ml (0.5 mmol, about 15 mol %) of a 5.4M solution of sodium methylate in methanol was added and the mixture was stirred at 50° C. for one hour [(tlc (SiO$_2$): R$_f$ (starting material)=about 0.4; R$_f$ (product)=0.5; toluene/ethyl acetate (9:1)].

Then the mixture was neutralized with 0.1 ml of acetic acid, stirred at 0° C. for 2 hours, filtered off under suction with a small amount of methanol/water (9:1) and washed with ice-cold methanol. After drying under a water-jet vacuum and subsequently under a high vacuum at room temperature there were obtained 1.62 g (90% yield) of 4'-apo-β-carotenal as dark crystals with m.p. 161–162° C.; content according to HPLC: 97.7%; UV (cyclohexane with 3% chloroform): 520 nm (shoulder, log $\epsilon$=5.01; $E_{1\ cm}^{1\%}$= 2100), 492 nm (log $\epsilon$=5.12; $E_{1\ cm}^{1\%}$= 2709), 296 nm (log $\epsilon$=4.44; $E_{1\ cm}^{1\%}$=566); $^1$H-NMR (400 MHz, CDCl$_3$): 9.35 ppm (C$\underline{H}$O); IR (KBr): 1670, 1611 cm$^{-1}$; mass spectrum: 482 (M$^+$, 30), 119 (100); microanalysis: Calc.: C 87.08% H 9.60% Found: C 86.60% H 9.56%.

EXAMPLE 16
4'-Apo-β-carotenal (through process from 8'-apo-β-carotenal dimethyl acetal and 1-methoxy-2-methyl-1,3-butadiene via 8'-methoxy-7',8'-dihydro-4'-apo-β-carotenal)

6.4 g (13.6 mmol) of 8'-apo-β-carotenal dimethyl acetal (content according to HPLC: about 98%) and 2.22 g (21.7 mmol, 1.6 eq.) of 1-methoxy-2-methyl-1,3-butadiene (GC: about 96%) were placed under argon in a 250 ml two-necked round flask equipped with a magnetic stirrer. 80 mg (0.4 mmol, 3 mol %) of p-toluenesulphonic acid monohydrate were added to the mixture at −15° C. and it was stirred at this temperature for 1½ hours [tlc (SiO$_2$) after prior hydrolysis: $R_f$ (acetal)=about 0.4; $R_f$ (product)=about 0.3; toluene/ethyl acetate (19:1)]. Then, for the hydrolysis, 20 ml of acetic acid/water (9:1) were added at −15° C. and the mixture was stirred at 0° C. for 2 hours. Subsequently, it was poured into water and extracted twice with 100 ml each time, a total of 200 ml, of ethyl acetate and concentrated. This gave 8.7 g of crude 8'-methoxy-7',8'-dihydro-4'-apo-β-carotenal as a red resin with a content of 91.6% according to HPLC.

This residue was now taken up without purification in 160 ml of methanol/ethyl acetate (3:1), with only a part of the residue being soluble, and the solution plus residue was treated with 1.4 ml (7.5 mmol, about 0.4 eq.) of a 5.4M solution of sodium methylate in methanol and stirred at 50° C. for 5 hours [tlc (SiO$_2$): $R_f$ (8'-methoxy- 7',8'-dihydro-4'-apo-β-carotenal)=about 0.3; $R_f$ (product)=about 0.5–0.6; toluene/ethyl acetate (19:1)].

Then the mixture was neutralized with 1.5 ml of acetic acid, cooled to 0° C., suction filtered and the filter material was washed with cold (0° C.) methanol/water (9:1) and cold methanol and dried to constant weight under a water-jet vacuum and under a high vacuum at room temperature. This gave 4.78 g (70% yield based on the 8'-apo-β-carotenal dimethyl acetal) of 4'-apo-β-carotenal as a dark violet powder with m.p. 142–145° C. and a content of 96% according to HPLC.

The further analytical data correspond to those which are present at the end of Example 15.

EXAMPLE 17
3',4'-Didehydro-β,ψ-caroten-16'-al 1.00 g (1.64 mmol) of 4'-methoxy-β,ψ-caroten-16'-al (content according to HPLC: 95.4%) in 14 ml of toluene/ethanol (1:1) was placed under argon in a 25 ml round flask. 0.1 ml (0.5 mmol, 30 mol %) of a 5.4M sodium methylate solution in methanol was added and the mixture was stirred at 35° C. for 3 hours [tlc (SiO$_2$): $R_f$=about 0.6; toluene/ethyl acetate (19:1)].

For the neutralization, 0.1 ml of acetic acid was added, the mixture was cooled to 0° C., filtered and the resulting crystals were washed with cold methanol and water. This gave, after drying under a high vacuum at room temperature, 880 mg (97% yield) of 3',4'-didehydro-β,ψ-caroten-16'-al (torularhodin aldehyde) as dark red crystals with m.p. 176–177° C. and a content according to HPLC of 99.2%.

UV (cyclohexane/3% chloroform): 514 nm (log $\epsilon$=5.19; $E_{1\ cm}^{1\%}$=2820), 326 nm (log $\epsilon$=4.55; $E_{1\ cm}^{1\%}$=644); $^1$H-NMR (250 MHz, CDCl$_3$): 9.45 ppm (C$\underline{H}$O); IR (KBr): 1660 cm$^{-1}$ (CHO); mass spectrum: 548 (M$^+$, 100).

Microanalysis: Calc.: C 87.53% H 9.55% Found.: C 87.41% H 9.35%.

EXAMPLE 18
Crocetin Dialdehyde 9.6 g (25.8 mmol) of 11,12,11',12'-tetrahydro-12,12'-dimethoxy-8,8'-diapocarotene-8,8'-dial(content according to HPLC: 97.1%) in 100 ml of methanol were placed under argon in a 250 ml round flask. 0.75 ml (3.9 mmol, 15 mol %) of a 5.4M sodium methylate solution in methanol was added at room temperature and the mixture was stirred at room temperature for 1 hour and at 35° C. for 2 hours [tlc (SiO$_2$): $R_f$=about 0.6 (product) and about 0.5 (starting material); toluene/ethyl acetate (19:1)].

For the neutralization, 5 ml of acetic acid were added thereto, the mixture was cooled to 0° C. and filtered, and the resulting red crystals were washed in sequence with 40 ml of methanol/water (9:1) at 0° C., 100 ml of water and again with 40 ml of methanol/water (9:1) at 0° C. After drying under a water-jet vacuum at 35° C. and under a high vacuum at room temperature there were obtained 6.99 g (91% yield) of crocetin dialdehyde as dark red, glistening crystals with m.p. 195–1960° C. and a content according to HPLC of 99.7%.

UV (cyclohexane/5% chloroform): 464 nm (log $\epsilon$=5.14), 436 nm (log $\epsilon$=5.13), 413 nm (log $\epsilon$=4.91); IR (KBr): 1668 cm$^{-1}$ (CHO); mass spectrum: 296 (M$^+$, 100); microanalysis: Calc.: C 81.04% H 8.16% Found: C 80.92% H 8.19%.

EXAMPLE 19
Crocetin dialdehyde (through process from C$_{10}$-dialdehyde dimethyl acetal and 1-methoxy-2-methyl-1,3-butadiene via 11,12,11',12'-tetrahydro-12,12'-dimethoxy-8,8'-diapocarotene-8,8'-dial)

25.74 g (100 mmol) of C$_{10}$-dialdehyde dimethyl acetal (content according to HPLC: 99.5%) in 250 ml of toluene were placed under argon in a 500 ml four-necked sulphonation flask equipped with a magnetic stirrer, a dropping funnel and a thermometer. At −25° C. there were then added 190 mg (1 mol %) of p-toluenesulphonic acid monohydrate, followed by a solution of 23.65 g (235 mmol, 2.35 eq.) of 1-methoxy-2-methyl-1,3-butadiene in 40 ml of toluene within 20 minutes at −25° C. The mixture was stirred at −25° C. for a further 45 minutes [tlc (SiO2) after prior hydrolysis: $R_f$=about 0.5 (product) and about 0.3 (acetal); toluene/ethyl acetate (4:1)].

Then, for the hydrolysis, 75 ml of acetic acid/water (9:1) were added at −25° C. and the reaction solution was stirred at room temperature for 2 hours. The subsequent working up was effected analogously to Example 7 or 8, which gave 42 g of crude 11,12,11',12'-tetrahydro-12,12'-dimethoxy-8,8'-diapocarotene-8,8'-dial as a yellow oil. This was taken up in 250 ml of methanol and the solution was treated while stirring with 2.75 ml (15 mol %) of a 5.4M sodium methylate solution in methanol. The mixture was stirred at 35° C. for 1½ hours [tlc (SiO$_2$): $R_f$=about 0.6 (product) and about 0.4 (intermediate); toluene/ethyl acetate (4:1)].

10 ml of acetic acid were added to the resulting red suspension. The mixture was cooled to −10° C., stirred at this temperature for 2 hours and the resulting red crystals were filtered off. Subsequently, the crystals were washed in sequence with 50 ml of methanol/water (9:1) at 0° C., 100 ml of water at room temperature and 50 ml of methanol/water (9:1) at 0° C. and dried to constant weight under a water-jet vacuum at 35° C. and under a high vacuum at room temperature. In this manner there were obtained 21.8 g (73% yield) of crocetin dialdehyde as dark red, glistening crystals with m.p. 193–194° C. and a content of 99.3% according to HPLC.

EXAMPLE 20

4,4'-Diapocarotenal 350 mg (0.75 mmol) of 7,8,7',8'-tetrahydro-8,8'-dimethoxy-4,4'-diapocarotin-4,4'-dial (content according to HPLC: 91.7%) in 18 ml of ethanol were placed under argon in a 25 ml round flask. 0.28 ml (1.5 mmol, 2 eq.) of a 5.4M sodium methoxide solution in methanol was added to the solution and the mixture was stirred at 50° C. for 3 hours. There was obtained a dark suspension [tlc (SiO$_2$): R$_f$=about 0.5 (product) and about 0.3 (starting material); toluene/ethyl acetate (9:1)].

After cooling the suspension to 0° C., filtering off the crystals, washing in sequence with 5 ml of methanol, 5 ml of water and 5 ml of methanol and drying under a high vacuum at room temperature there were obtained 295 mg (88% yield) of 4,4'-diapocarotenal as dark blue crystals with m.p. 226° C. and a content of 96.3% according to HPLC.

UV (cyclohexane/2% chloroform): 537 nm (log $\epsilon$=5.14; $E_{1\ cm}^{1\%}$=3190), 501 nm (log $\epsilon$=5.20; $E_{1\ cm}^{1\%}$=3700), 471 nm (log $\epsilon$=5.04; $E_{1\ cm}^{1\%}$=2565); IR (KBr): 1680 cm$^{-1}$ (CHO); mass spectrum: 428 (M$^+$, 100).

Upon reading the present specification, various alternative embodiments will become obvious to the skilled artisan. These variations are to be considered within the scope and spirit of the invention which should only be limited by the claims that follow and their equivalents.

What is claimed is:

1. A process for manufacturing a compound of the formula:

$$A-CH=CH-\underset{\underset{R^2}{|}}{\overset{\overset{R^1}{|}}{C}}=C-CHO \qquad \text{I'}$$

or $$OHC-\underset{\underset{R^2}{|}}{\overset{\overset{R^1}{|}}{C}}=C-HC=HC-B-CH=CH-\underset{\underset{R^2}{|}}{\overset{\overset{R^1}{|}}{C}}=C-CHO \qquad \text{I''}$$

wherein

A is a monovalent conjugated polyene group or a methyl-substituted, monovalent conjugated polyene group, B is a bivalent conjugated polyene group or a methyl-substituted, bivalent conjugated polyene group and R$^1$ and R$^2$ each independently is hydrogen or methyl, with the —CH=CH—C(R$^1$)=C(R$^2$)—CHO group(s) in each case being situated in the terminal position(s) of the conjugated chain of group A or B, which process comprises:

(A) reacting a compound of formula:

$$A-CH(OR^3)_2 \qquad \text{II'}$$

or $$(R^3O)_2HC-B-CH(OR^3)_2 \qquad \text{II''}$$

wherein

A and B are as above, with the —CH(OR$^3$)$_2$ group(s) being situated in the terminal position(s) of the conjugated chain of group A or B, and R$^3$ is C$_{1-6}$-alkyl, with a compound of formula:

$$CH_2=\underset{\underset{R^2}{|}}{\overset{\overset{R^1}{|}}{C}}-C=CH-OR^4 \qquad \text{III}$$

wherein

R$^1$ and R$^2$ are as above, and

R$^4$ is C$_{1-6}$-alkyl, in the presence of a Brönsted acid to form an intermediate;

(B) hydrolyzing the intermediate to form a compound of formula:

$$A-\underset{}{\overset{\overset{OR^3}{|}}{CH}}-CH_2-\underset{\underset{R^2}{|}}{\overset{\overset{R^1}{|}}{C}}=C-CHO \qquad \text{IV'}$$

or $$OHC-\underset{\underset{R^2}{|}}{\overset{\overset{R^1}{|}}{C}}=C-H_2C-\overset{\overset{R^3O}{|}}{HC}-B-\overset{\overset{OR^3}{|}}{CH}-CH_2-\underset{\underset{R^2}{|}}{\overset{\overset{R^1}{|}}{C}}=C-CHO \qquad \text{IV''}$$

wherein

A, B, R$^1$, R$^2$ and R$^3$ are as above, with the —CH(OR$^3$)—CH$_2$—C(R$^1$)=C(R$^2$)—CHO group(s) being situated in the terminal position(s) of the conjugated chain of group A or B; and (C) cleaving off the alcohol R$^3$OH from the compound of formula IV' or IV'' in the presence of an alkali metal alcoholate.

2. The process according to claim 1, wherein the reacting involves a compound of formula:

$$R-CH(OR^3)_2 \qquad \text{II}$$

wherein

R is a group (a), (b) or (c)

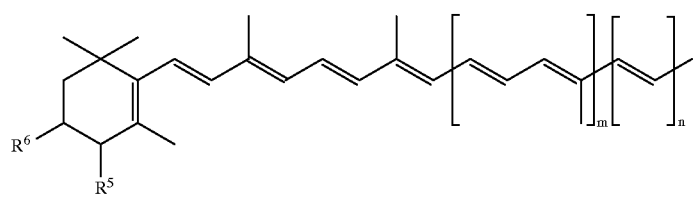

(a)

-continued

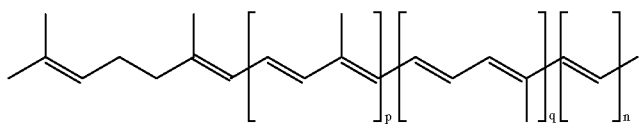
(b)

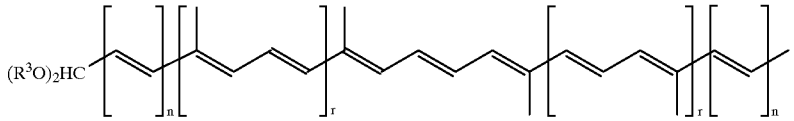
(c)

in which
R³ is C$_{1-4}$-alkyl,
R⁵ and R⁶ each independently is hydrogen, a hydroxy group, a protected hydroxy group, an oxo group, or a protected oxo group,
m is 0, 1, 2, 3 or 4,
n is 0 or 1,
p is 0, 1 or 2,
q is 0, 1, 2 or 3 and
r is 0, 1 or 2,
and is converted after carrying out the multistage process defined in claim 1 into the corresponding product of formula:

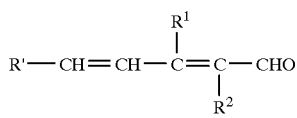   I wherein R' is a group (a) or (b), or a group (c')

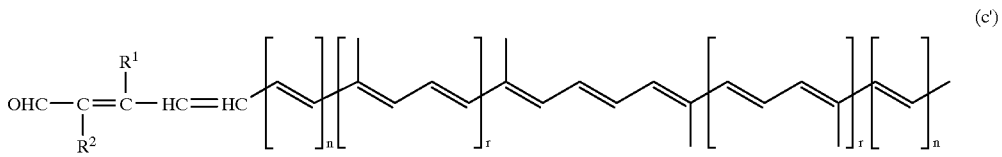
(c')

3. The process according to claim 2, wherein where a group (a) is present in the product of formula I and a protecting group is present, the protecting group is cleaved off.

4. The process according to claim 2, wherein R is a group (a) in which R⁵ and R⁶ both are hydrogen and n is 0, or R is a group (c) in which both n's are 0 and R¹ and R² are hydrogen and methyl, respectively.

5. The process according to claim 1, wherein the reacting is in the presence of a Brönsted acid selected from the group consisting of p-toluenesulphonic acid, methanesulphonic acid, trifluoromethanesulphonic acid, sulphuric acid, and trifluoroacetic acid.

6. The process according to claim 5, wherein the Brönsted acid is used in a catalytic amount which is between about 0.5 and 5 mol % based on the amount of the compound of formula II' or II" as appropriate.

7. The process according to claim 1, wherein about 1.05 to about 1.6 equivalents of the compound of formula III are reacted per equivalent of the compound of formula II' or about 2.1 to about 3.2 equivalents of the compound of formula III are reacted per equivalent of the compound of formula II'.

8. The process according to claim 1, wherein the compound of formula II' or II", as appropriate, is reacted with the compound of formula III in an organic solvent at temperatures in the range of about −60° C. to about +60° C., with an organic solvent selected from the group consisting of a lower aliphatic hydrocarbon, a cyclic hydrocarbon, a lower halogenated aliphatic hydrocarbon, a lower aliphatic ether, a cyclic ether, a lower aliphatic nitrile, and an aromatic.

9. The process according to claim 8, wherein the reacting is in an organic solvent selected from the group consisting of n-pentane, n-hexane, cyclohexane, methylene chloride, chloroform, diethyl ether, tert.butyl methyl ether, tetrahydrofuran, acetonitrile and toluene, and the reaction is effected in the temperature range of from about −20° C. to room temperature.

10. The process according to claim 1, wherein immediately after completion of the reaction of formula II' or II", as appropriate, with the compound of formula III, the intermediate resulting therefrom is itself hydrolyzed in a reaction mixture by adding to the reaction mixture an aqueous solution of a weak acid and subsequently stirring the mixture in the temperature range of from about 0° C. to room temperature.

11. The process of claim 10, wherein the weak acid is dilute acetic acid.

12. The process according to claim 1, wherein the cleavage of the alcohol R³OH from the compound of formula IV' or IV" is carried out by reacting the compound of formula IV' or IV" dissolved in an organic solvent in the presence of a catalytic amount of an alkali alcoholate selected from the group consisting of sodium methylate, sodium ethylate, potassium methylate, potassium ethylate, and potassium tert.butylate.

13. A compound of formula:

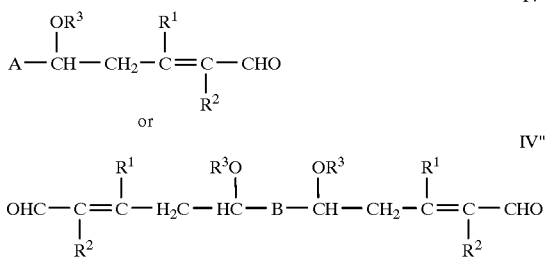

wherein

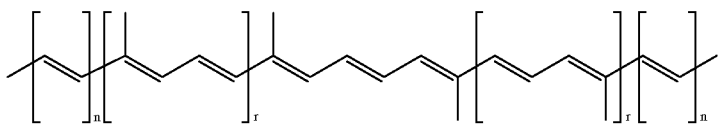

A is a monovalent conjugated polyene group or a methyl-substituted, monovalent conjugated polyene group, B is a bivalent conjugated polyene group or a methyl-substituted, bivalent conjugated polyene group, $R^1$ and $R^2$ each independently is hydrogen or methyl, and $R^3$ is $C_{1-6}$-alkyl, with the —CH(OR$_3$)—CH$_2$—C(R$^1$)=C(R$^2$)—CHO group(s) in each case being situated in the terminal position(s) of the conjugated chain of group A or B.

14. The compound of claim 13, wherein the compound is of formula IV' and A is a group

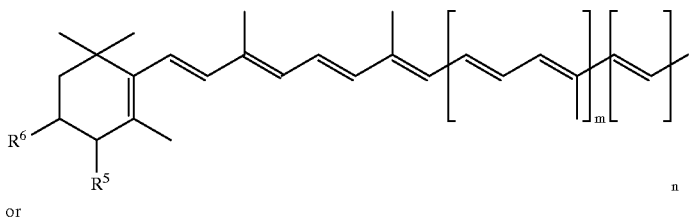

in which $R^5$ and $R^6$ each independently is hydrogen, a hydroxy group, a protected hydroxy group, an oxo group, or a protected oxo group, m is 0, 1, 2, 3 or 4, n is 0 or 1, p is 0, 1 or 2, and q is 0, 1, 2 or 3.

15. The compound of claim 13, wherein the compound is of the formula IV" and

B is a group

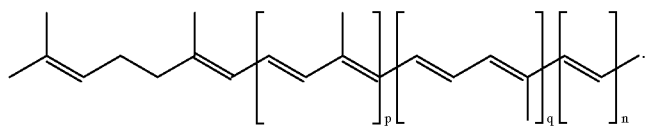

in which n is 0 or 1, and r is 0 or 1.

16. The compound according to claim 13, which is 15-methoxy-15,15'-dihydro-12' apo-β-carotenal.

17. The compound according to claim 13, which is 12'-methoxy-11',12'-dihydro-8'-apo-β-carotenal.

18. The compound according to claim 13, which is 8'-methoxy-7',8'-dihydro-4'-apo-β-carotenal.

19. The compound according to claim 13, which is 4'-methoxy-β,ψ-caroten-16'-al.

20. The compound according to claim 13, which is 11,12,11',12'-tetrahydro-12,12'-dimethoxy-8,8'-diapocarotene-8,8'-dial.

21. The compound according to claim 13, which is 7,8,7',8'-tetrahydro-8,8'-dimethoxy-4,4'-diapocarotene-4,4'-dial.

* * * * *